(12) United States Patent
Lebedev et al.

(10) Patent No.: US 6,482,983 B1
(45) Date of Patent: Nov. 19, 2002

(54) PROCESS FOR OBTAINING N-MONOSUBSTITUTED AMIDES

(75) Inventors: Mikhail Yu. Lebedev, Jacksonville, FL (US); Mark B. Erman, Atlantic Beach, FL (US)

(73) Assignee: Millennium Specialty Chemicals, Jacksonville, FL (US)

( * ) Notice: Subject to any disclaimer, the term of this patent is extended or adjusted under 35 U.S.C. 154(b) by 0 days.

(21) Appl. No.: 09/919,379

(22) Filed: Jul. 31, 2001

(51) Int. Cl.[7] .............................................. C07C 231/06
(52) U.S. Cl. ...................................... 564/129; 564/124
(58) Field of Search ................................. 564/129, 124

(56) References Cited

U.S. PATENT DOCUMENTS

| | | | |
|---|---|---|---|
| 4,246,199 A | * 1/1981 | Arlt et al. | ..................... 564/124 |
| 5,712,413 A | 1/1998 | Burrington et al. | |
| 5,811,580 A | 9/1998 | Rhubright | |
| 6,303,817 B1 | * 10/2001 | Boden et al. | ................ 564/124 |

FOREIGN PATENT DOCUMENTS

EP 846 678 A1 6/1998

OTHER PUBLICATIONS

Barton, D.H.R. et al. Conversion of Alcohols into Amides by Chlorodiphenylmethylium Hexachloroantimonate in Nitrile Solvents; Some Further Reactions of the Triphenylmethyl Cation. *J. Chem. Soc. Perkin I* 2101–2107 (1974).

Benson, F.R. et al. A New Reaction of Nitriles. III. Amides from Dinitriles. *J. Amer. Chem. Soc.* 71:4128–4129 (1949).

Bishop, R. Ritter–type Reactions *Comprehensive Organic Synthesis* 6:261–300 (1991).

Buc S.R. The Reaction of N–Hydroxymethyl Phthalimide with Nitriles. *J. Amer. Chem. Soc.* 69:254–256 (1947).

Chen, H.G. et al. A Novel Modification of the Ritter Reaction Using Trimethylsilyl Cyanide. *Tetrahedron Lett.* 37:8129–8132 (1996).

Firouzabadi, H. et al. Highly Selective amidation of Benzylic Alcohols With Nitriles. A Modified Ritter Reaction. *Synth. Commun.* 24:601–607 (1994).

Kiersznicki, T. et al. The Synthesis of N–(η–Alkyl)–Amides in the Reaction of Alcohols or Their Dichlorophosphates with Nitriles, *Rocz. Chem.* 51:1021–1026 (1977).

Kumar et al. Clay catalysed amidation of alcohols with nitriles in dry media. *New J. Chem.* 23:955–956 (1999).

Magat, E.E. Acid–catalyzed Reactions of Nitriles. III. The Reaction of Nitriles with N–Methylolamides. *J. Amer. Chem. Soc.* 73:1035–1036 (1951).

Martinez, A.G. et al. An Improved Modification of Ritter Reaction. *Tetrahedron Lett.* 30:581–582 (1999).

Parris et al. N–Alkylation of Nitriles with Benzyl Alcohol, Related Alcohols, and Glycols. *J. Org. Chem.* 25:331–334 (1960).

Ritter, J.J. et al. A New Reaction of Nitriles. I. Amides from Alkenes and Mononitriles. *J. Amer. Chem. Soc.* 70:4045–4050 (1948).

Sanguigni, J.A. et al. Amides from nitriles and alcohols by the Ritter reaction. *J. Med. Chem.* 7:573–574 (1964) (Abstract).

Sasaki et al. Synthesis of Adamantane Derivatives. IX. The Ritter Reaction of 1–Hydroxymethyladamantane with Acetonitrile. *Bull. Chem. Soc. Japan* 43:1820–1824 (1970).

* cited by examiner

Primary Examiner—Shailendra Kumar
(74) Attorney, Agent, or Firm—Needle & Rosenberg, P.C.

(57) ABSTRACT

A process for obtaining an amide of the general formula R—(CO)—NH—CH$_2$—X involves contacting a nitrile of the general formula R—CN with:

a) an acid; and c) an alkoxy-containing compound comprising at least one alkoxy functionality of the general formula —OCH$_2$—X;

wherein R is hydrogen or an alkyl, cycloalkyl, alkenyl, cycloalkenyl, alkynyl, aryl, or heterocyclic substituent, which substituents can be substituted or unsubstituted; wherein X is hydrogen or a radical having the general formula —CHR$^1$R$^2$; and wherein R$^1$ and R$^2$ independently or collectively represent hydrogen or an alkyl, cycloalkyl, alkenyl, cycloalkenyl, alkynyl, aryl, or heterocyclic substituent, or any combination thereof, which substituents can be substituted or unsubstituted. Moreover, the inventive process can involve other similar reactions, for example, at least one nitrile can be reacted with a reagent comprising both (i) at least one suitable alkoxy functionality; and (ii) at least one suitable acid functionality.

31 Claims, No Drawings

PROCESS FOR OBTAINING N-MONOSUBSTITUTED AMIDES

FIELD OF THE INVENTION

The present invention relates to a process for obtaining N-monosubstituted amides, which are useful as synthetic intermediates in practically all branches of organic chemistry, and many of which are also important as compounds possessing biological and physiological activity, including a physiological cooling effect for cosmetics, flavorings and other applications.

BACKGROUND OF THE INVENTION

Among numerous known methods for obtaining N-monosubstituted amides, the Ritter reaction has long been considered to be one of the simplest processes based on readily available reagents, e.g., nitrites, sulfuric acid, olefins, alcohols, aldehydes, and/or other potential donors of a carbenium ion.

In their original experiments, Ritter and coworkers added olefins to a mixture of sulfuric acid and acetonitrile in glacial acetic acid as a solvent and, after a simple workup, obtained N-monosubstituted amides in relatively good yields (J. J. Ritter and P. P. Minieri, J. Amer. Chem. Soc., 1948, Vol. 70, pp. 4045–4048). In a number of following publications, they also used tertiary and secondary alcohols as donors of a carbenium ion, and found that secondary alcohols required harsher conditions, e.g., concentrated sulfuric acid as the reaction medium instead of dilution with acetic acid (J. J. Ritter and J. Kalish, J. Amer. Chem. Soc., 1948, Vol. 70, pp. 4048–4049; F. R. Benson and J. J. Ritter, ibid., 1949, Vol. 71, pp. 4128–4129). It was found that primary alcohols did not react, even under harsher reaction conditions. In fact, as stated in the latter reference, "Efforts to utilize a primary alcohol in the reaction proved fruitless; expedients such as the use of elevated temperatures, prolonged heating or the employment of fuming sulfuric acid were unsuccessful in the production of N-primary alkyl amides."

Certain limited exceptions to that general rule have been reported. See, for example, Table 1. In all cases, an excess of nitrile has been used with respect to the alcohol.

TABLE 1

Limited exceptions to general rule

| Nitrile, moles | Alcohol, moles | Molar ratio Nitrile/Alcohol/Sulfuric Acid | Yield, % crude/recrystallized | Reference |
|---|---|---|---|---|
| MeCN, 3.8 | Benzyl alcohol, 1.0 | 3.8/1/1.41 | –/48 | C. L. Parris and R. M. Christenson, J. Org. Chem., 1960, Vol. 25, pp. 331–334 |
| CH$_2$=CHCN, 3.8 | Benzyl alcohol, 1.0 | 3.8/1/1.41 | –/50 | C. L. Parris and R. M. Christenson, J. Org Chem., 1960, Vol. 25, pp. 331–334 |
| CH$_2$=CHCN 3.8 | Benzyl alcohol, 1.0 | 3.8/1/1.41 | –/59–62 | C. L. Parris, Organic Syntheses, 1962, Vol. 42, pp. 16–18 |
| MeCN. 3.8 | p-Methyl benzyl alcohol, 1.0 | 3.8/1/1.41 | –/40 | C. L. Parris and R. M. Christenson, J. Org. Chem., 1960, Vol. 25, pp. 331–334 |
| MeCN, 0.96 | Benzyl alcohol, 0.2 | 0.96/0.2/0.2 | –/72.5 | J. A. Sanguigni and R. Levins, J. Med. Chem., 1964, Vol. 7, pp. 573–574 |
| EtCN | Benzyl alcohol, 0.2 | 0.96/0.2/0.2 | –/45 | J. A. Sanguigni and R. Levins, J. Med. Chem., 1964, Vol. 7, pp. 573–574 |
| CH$_2$=CHCN | Benzyl alcohol | 0.96/0.2/0.2 | –/50 | J. A. Sanguigni and R. Levins, J. Med. Chem., 1964, Vol. 7, pp. 573–574 |
| PhCH$_2$CN | Benzyl alcohol | 0.96/0.2/0.2 | –/27 | J. A. Sanguigni and R. Levins, J. Med. Chem., 1964, Vol. 7, pp. 573–574 |
| PhCN | Benzyl alcohol | 0.96/0.2/0.2 | –/55 | J. A. Sanguigni and R. Levins, J. Med. Chem., 1964, Vol. 7, pp. 573–574 |
| MeCN, 76.5 | Hydroxymethyl adamantane, 1.2 | 76.5/1.2/28 | 92/36.7 | Sasaki et al. Bull. Chem. Soc. Japan, 1970, Vol. 43, pp. 1820–1824 |
| MeCN, 76.5 | Hydroxymethyl adamantane, 1.2 | 76.5/1.2/28 +26 acetic acid | trace | Sasaki et at Bull. Chem. Soc. Japan, 1970, Vol. 43, pp. 1820–1824 |
| MeCN, 0.134 | N-methylol phthalimide, 0.1 | 0.13/0.1/0.94 | 93/83 | S. R. Buc. J. Amer. Chem. Soc., 1947, Vol. 69, pp. 254–256 |
| NCCH$_2$COOH, 0.12 | N-methylol phthalimide, 0.1 | 0.12/0.1/0.94 | 96/91 | S. R. Buc. J. Amer Chem. Soc., 1947, Vol. 69, pp 254–256 |
| PhCN, 0.108 | N-methylol phthalimide, 0.1 | 0.11/0.1/0.94 | 96.5/77.5 | S. R. Buc. J. Amer. Chem. Soc., 1947, Vol. 69, pp. 254–256 |
| CH$_2$=CHCN, 0.07 | N-methylol benzamide, 0.05 | 0.07/0.05/0.94 | –/60 | E. E. Magat & L. F. Salisbury, J. Amer.Chem. Soc., 1951, Vol. 73, pp. 1035–1036 |

The occurrence of very poor yields of amide formation, or even a total inability of methanol and other lower primary alcohols to take part in the "classic" Ritter reaction has frequently been confirmed in later publications and reviews.

See, for example: D. H. R. Barton et al., J. Chem. Soc. Perkin I, 1974, pp. 2101–2107; T. Kiersznicki and R. Mazurkiewicz, Rocz. Chem., 1977, Vol. 51, pp.1021–1026; A. G. Martinez et al., Tetrahedron Lett., 1989, Vol. 30, pp. 581–582; R. Bishop, Ritter-type Reactions. In: Comprehensive Organic Synthesis, eds. B. M. Trost and I. Fleming, Pergamon Press, Oxford, 1991, Vol. 6, pp. 261–300; H. Firouzabadi et al., Synth. Commun., 1994, Vol. 24, pp. 601–607; and H. G. Chen et al., Tetrahedron Lett., 1996, Vol 37, pp. 8129–8132, each of which are incorporated by reference.

Several "non-classic" Ritter reaction modifications have been developed in order to attempt to obtain N-primary alkyl amides. For instance, n-decanol (0.95 mmol) and acetonitrile (96 mmol) in the presence of 3.4 mmole of dichloro (phenyl)methylium hexachloroantimonate gave N-decylacetamide in 60% yield (D. H. R. Barton et al., J. C. S. Perkin I, 1974, pp. 2101–2107). Similarly, the addition of 10 mmoles of ethanol or butanol to a mixture of 10 mmoles of trifluoromethanesulfonic anhydride and a double excess of acetonitrile or benzonitrile gave 80–90% yield of the corresponding N-alkylamides (A. G. Martinez et al., Tetrahedron Lett., 1989, Vol. 30, pp. 581–582). However, use of such "exotic" and costly reagents as these, makes these modifications industrially impractical.

Patents relating to processes for obtaining N-hydrocarbyl substituted amides include U.S. Pat. No. 5,811,580; EP846, 678 A1; and U.S. Pat. No. 5,712,413.

Finally, an article describing clay (Montmorillonite KSF) catalyzed amidation of alcohols, a primary aliphatic alcohol n-octanol was reported inactive (H. M. Sampar Kumar et al., New J. Chem., 1999, Vol. 23, pp. 955–956).

Thus, it is clear that the need still exists for an economically feasible and practical method for obtaining N-monosubstituted amides by a Ritter type reaction of nitrites with primary aliphatic alcohols or other compounds containing primary alkoxy groups.

SUMMARY OF THE INVENTION

Among other aspects, the present invention relates to the surprising discovery of an improved process for obtaining N-primary alkyl monosubstituted amides, cyclic amides or lactams, functionally substituted diamides and polyamides, and cyclic polyamides using relatively inexpensive and readily available reagents including nitrites, acids and primary alkoxy compounds such as lower primary alkohols.

In one embodiment, the present invention relates to a process for obtaining an amide of the general formula R—(CO)—NH—CH$_2$—X, said process comprising contacting a nitrile of the general formula R—CN with:

a) an acid; and
b) an alkoxy-containing compound comprising at least one alkoxy functionality of the general formula —OCH$_2$—X;

wherein R is hydrogen or an alkyl, cycloalkyl, alkenyl, cycloalkenyl, alkynyl, aryl, or heterocyclic substituent, which substituents can be substituted or unsubstituted; wherein X is hydrogen or a radical having the general formula —CHR$^1$R$^2$; and wherein R$^1$ and R$^2$ independently or collectively represent hydrogen or an alkyl, cycloalkyl, alkenyl, cycloalkenyl, alkynyl, aryl, or heterocyclic substituent, or any combination thereof, which substituents can be substituted or unsubstituted.

In addition, the process of the present invention comprises reacting at least one nitrile with a reagent comprising both (i) at least one suitable alkoxy functionality; and (ii) at least one suitable acid functionality.

For example, the present invention includes a process for obtaining an amide of the general formula R—(CO)—NH—CH$_2$—X, said process comprising contacting a nitrile of the general formula R—CN with a monoalkylsulfate of the general formula X—CH$_2$—O–SO$_3$H, wherein R is again selected from hydrogen or an alkyl, cycloalkyl, alkenyl, cycloalkenyl, alkynyl, aryl, or heterocyclic substituent, which substituent can be substituted or unsubstituted; and wherein X is selected from hydrogen or a radical having the general formula —CHR$^1$R$^2$, wherein R$^1$ and R$^2$ individually or collectively represent hydrogen or an alkyl, cycloalkyl, alkenyl, cycloalkenyl, alkynyl, aryl, or heterocyclic substituent, or any combination thereof, and which substituents can again be substituted or unsubstituted.

In another example, the present invention provides a process for obtaining an amide of the general formula R—(CO)—NH—CH$_2$—X, said process comprising contacting a nitrile of the general formula R—CN with one or more acid phosphates, e.g., monoalkyl phosphates; dialkyl phosphates; mono, di, and trialkyl pyrophosphates; and mono-, di-, tri, and polyalkyl polyphosphates and the like, comprising at least one alkoxy functionality of the generic formula XCH$_2$—O— and one or more acid phosphate functionalities of the generic formula:

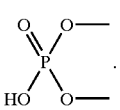

(V)

Additional advantages and embodiments of the invention will be obvious from the description, or may be learned by practice of the invention. Further advantages of the invention will also be realized and attained by means of the elements and combinations particularly pointed out in the appended claims. Thus, it is to be understood that both the foregoing general description and the following detailed description are exemplary and explanatory of certain embodiments of the invention, and are therefore not restrictive of the invention as claimed.

DETAILED DESCRIPTION OF THE INVENTION

The present invention may be understood more readily by reference to the following detailed description, including any figures, tables and examples provided herein. It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular forms "a", "an", and "the" comprise plural referents unless the context clearly dictates otherwise. For example, reference to a component in the singular is intended to comprise a plurality of components.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about" or "approximately," it will be understood that the particular value forms another embodiment.

The term "alkyl," as used herein, refers to a branched or unbranched, cyclic or acyclic saturated hydrocarbon group, including without limitation, such examples as methyl, ethyl, n-propyl, isopropyl, butyl, isobutyl, tert-butyl, cyclohexyl, p-menthyl, octyl, eicosyl, tetracosyl and the like.

The term "alkoxy," as used herein, refers to a hydrocarbon group bound to an organic or inorganic molecule through an "—O—" ether linkage. For example, as used herein, an "alkoxy" group may be defined as —OR wherein R represents an alkyl group.

The term "alkenyl," as used herein, refers to a hydrocarbon group containing at least one double bond.

The term "alkynyl," as used herein, refers to a hydrocarbon group containing at least one triple bond.

The term "aryl," as used herein, refers to a hydrocarbon group having the ring structure characteristic of benzene, naphthalene, and anthracene; i.e., a hydrocarbon group having either the aromatic six carbon ring of benzene or the fused six carbon rings of the other aromatic derivatives. For example, an aryl group as used herein may include, without limitation, a phenyl $C_6H_5$ or naphthyl $C_{10}H_7$ group.

The terms "heterocycle" and/or "heterocyclic," as used herein, designate a closed ring structure, usually of five, six, or seven members, in which one or more of the atoms in the ring is a heteroatom such as sulfur, nitrogen, oxygen, and the like. Suitable examples include, without limitation, pyridine, pyrrole, furan, thiophene, tetrahydrofuran, and piperidine.

The term "functionally substituted," as used herein, means that the group or moiety of concern contains one or more functional groups (functional substituents) or any other heteroatomic groups. Such examples include, without limitation, carbonyl group(s), hydroxy groups, cyano groups, alkoxy groups, carboxy group(s), alkoxycarbonyl group(s), amino group(s), nitro group(s), nitroso group(s), halogen group(s) (e.g., chloro, fluoro or bromo groups), siloxy group(s), and the like.

As used herein with respect to any particular chemical formula, "Me" refers to a methyl group, "Et" refers to an ethyl group, "Bu" refers to a butyl group, and "Ph" refers to a phenyl group.

The present invention relates to a process for obtaining N-monosubstituted amides, cyclic amides or lactams, functionally substituted diamides and polyamides, and cyclic polyamides. To this end, contrary to the teachings of the prior art, it has been discovered that these amides can be obtained by reacting two or more reagents which independently or collectively provide at least one nitrile functionality, at least one alkoxy functionality, and at least one suitable acid functionality, in an environment suitable for amide formation.

In a first aspect, the present invention provides a process for obtaining N-monosubstituted amides having the generic formula (I):

R—CO—NH—CH$_2$X (I)

wherein R is a hydrogen or any alkyl, cycloalkyl, alkenyl,, cycloalkenyl, alkynyl, aryl, or heterocyclic substituent, which substituent can be substituted or unsubstituted, and wherein X is a hydrogen or a radical having the general formula —CHR$^1$R$^2$ wherein R$^1$ and R$^2$ independently or collectively represent hydrogens or any alkyl, cycloalkyl, alkenyl, cycloalkenyl, alkynyl, aryl, or heterocyclic substituent(s), or any combination thereof, which substituent(s) can also be functionally substituted or unsubstituted.

In one embodiment, the process comprises reacting: (1) at least one nitrile having the generic formula (II):

R—CN (II)

wherein R is a hydrogen or any alkyl, cycloalkyl, alkenyl, cycloalkenyl, alkynyl, aryl, or heterocyclic substituent, which substituents can be substituted or unsubstituted; with (2) at least one alkoxy compound comprising at least one suitable alkoxy functionality of the generic formula (III):

—O—CH$_2$—X (III)

wherein X is a hydrogen or a radical having the general formula —CHR$^1$R$^2$ wherein R$^1$ and R$^2$ independently or collectively represent hydrogens or any alkyl, cycloalkyl, alkenyl, cycloalkenyl, alkynyl, aryl, or heterocyclic substituent(s), or any combination thereof, which substituent(s) can again be functionally substituted or unsubstituted; in the presence of (3) a suitable acid.

In an alternative embodiment, the process of the present invention comprises reacting at least one nitrile, including that having the generic formula (II) as defined above, with a reagent comprising both (i) at least one suitable alkoxy functionality (III), as defined above; and (ii) at least one suitable acid functionality. To this end, there are numerous classes of compounds that combine the properties of both an alkoxy-containing compound and a suitable acid.

An example of such a preferred class of compounds according to the present invention includes, without limitation, alkyl sulfates, e.g., monoalkylsulfates such as, methylsulfuric acid, ethylsulfuric acid, butylsulfuric acid and the like, having the generic formula (IV):

X—CH$_2$—O—SO$_2$OH (IV)

wherein X is a hydrogen or a radical having the general formula —CHR$^1$R$^2$ wherein R$^1$ and R$^2$ independently or collectively represent hydrogens or any alkyl, cycloalkyl, alkenyl, cycloalkenyl, alkynyl, aryl, or heterocyclic substituent(s), or any combination thereof, which substituent(s) can also be functionally substituted or unsubstituted Another example of a class of compounds comprising both (i) at least one suitable alkoxy functionality (III), as defined above; and (ii) at least one suitable acid functionality includes, without limitation, acid alkyl phosphates. For example, monoalkyl phosphates; dialkyl phosphates; mono, di, and trialkyl pyrophosphates; and mono-, di-, tri, and polyalkyl polyphosphates and the like comprising at least one alkoxy functionality of the generic formula XCH$_2$—O— and one or more acid phosphate functionalities of the generic formula (V):

(V)

In accordance with this embodiment, X again represents either a hydrogen or a radical having the general formula —CHR$^1$R$^2$ wherein R$^1$ and R$^2$ independently or collectively represent hydrogens or any alkyl, cycloalkyl, alkenyl, cycloalkenyl, alkynyl, aryl, or heterocyclic substituent(s), or any combination thereof, which substituent(s) can be functionally substituted or unsubstituted.

To this end, it should be understood that the process of the present invention encompasses any appropriate combination for reacting two or more reagents independently or collectively comprising at least one suitable nitrile functionality, at least one suitable alkoxy functionality, and at least one suitable acid functionality in an environment suitable to provide a desired n-monosubstituted amide, cyclic amide (lactam), and/or polyamide. Furthermore, in accordance with several embodiments of the present invention, when one or more reactant(s) provides more than one of the necessary functionalities, e.g., nitrile, alkoxy, and/or acid, it should also be understood that the third reactant can still be present but is not required in order to effectively practice the process of the present invention. For example, in the case of a monoalkylsulfate being reacted with a suitable nitrile, the monoalkylsulfate comprises both an alkoxy and an acid functionality and, as such, a separate acid reagent and/ or a separate alkoxy reagent can be introduced into the reaction environment but is not required in order to successfully practice the invention.

In another aspect of N-monosubstituted amide group formation, the present invention further provides a process for obtaining cyclic amides, or lactams. In accordance with this aspect, when a single reagent provides at least one suitable nitrile functionality and at least one suitable alkoxy functionality, an intramolecular reaction may be provided in the presence of a suitable acid under conditions suitable to provide a cyclic amide or lactam.

In yet another aspect, the present invention also provides a process for obtaining functionally substituted amides and polyamides. For example, in one embodiment, when a single reagent provides at least one suitable nitrile functionality and at least one suitable alkoxy functionality, an intermolecular reaction may be provided in the presence of a suitable acid under conditions effective to provide, e.g., a cyano hydroxy amide, a cyano hydroxy diamide, or a cyano hydroxy polyamide.

In still another aspect, the process of amide formation according to the present invention comprises contacting one or more reagents having at least two suitable nitrile functionalities with one or more reagents comprising at least two suitable alkoxy functionalities. In accordance with this aspect of the invention, an intermolecular reaction may be provided in the presence of a suitable acid under conditions effective to provide, e.g., a cyano hydroxy amide, a cyano hydroxy diamide, a dicyano diamide, a dihydroxy diamide, a cyano hydroxy polyamide, a dicyano polyamide, a dihydroxy polyamide, and/or a cyclic polyamide.

According to the invention, a wide variety of inorganic and/or organic, Bronsted or Lewis acids can be used in this process. Furthermore, these acids can be used in their concentrated or diluted forms.

Examples of suitable Bronsted acids include, but are not limited to: sulfuric acid, fuming sulfuric acid, methylsulfuric acid or monomethyl sulfate, phosphoric acid, pyrophosphoric acid, polyphosphoric acid, chlorosulfonic acid, methane sulfonic acid, benzenesulfonic acid, p-toluenesulfonic acid, benzene disulfoacid, and trifluoromethylsulfonic acid.

Examples of suitable Lewis acids include, but are not limited to: sulfur trioxide or its complexes, boron trifluoride, aluminum chloride, aluminum bromide, and the like.

Suitable compounds comprising at least one alkoxy functionality of formula (III) as previously defined herein include without limitation, primary alcohols, such as methanol, ethanol, n-propanol, 1-butanol, 2-methyl-l-propanol, and dodecanol; glycols, such as ethylene glycol; di-, tri-, and polyglycols, such as diethylene glycol and/or polyethylene glycol; monoalkyl ethers of glycols, such as methylcellosolve; esters and orthoesters, such as dimethyl carbonate, ethyl formate, methyl acetate, diethyl malonate, and methylacetoacetate; alkyl orthocarbonates, such as methyl orthocarbonate; mono, di and tri alkyl carbonates, such as dimethyl carbonate; mono, di, and tri alkyl borates, such as trimethyl borate; mono, di and tri alkoxy silanes, such as tetraethoxysilane; alkyl orthosilicates, such as ethylorthosilicate; mono, di, tri and tetra alkoxy titanium compounds, such as tetraethoxy titanium; alkyl orthotitanates, such as methyl, ethyl, propyl or butyl ortho titanate; acid alkyl phosphates; mono, di and tri alkyl phosphates, such as trimethyl phosphate; mono, di and tri alkyl pyrophosphates, such as dimethyl pyrophosphate; alkyl polyphosphates; dialkyl sulfates, such as dimethylsulfate; alkyl sulfates, such as mono methyl, ethyl, propyl or butyl sulfate; alkyl halo sulfates, such as alkyl chlorosulfates and alkyl bromosulfates; alkyl mesylates; alkyl aryl sulfonates; ethers and dialkyl ethers, such as methyl ether and butyl ether; glycol ethers; aryl alkyl ethers; acetals, ketals, dialkyl acetals and dialkyl ketals, such as dimethoxymethane; alkyl esters, and any functionally substituted primary alcohols, glycols, esters, orthoesters, acetals or ketals.

To this end, it should be understood that any alkoxy containing compound suitable for amide formation can be used in the process of the present invention, provided that said compound comprises at least one suitable alkoxy functionality of the generic formula (III):

$$—O—CH_2—X \quad (III)$$

wherein X is a hydrogen or a radical having the general formula $—CHR^1R^2$ wherein $R^1$ and $R^2$ independently or collectively represent hydrogens or any alkyl, cycloalkyl, alkenyl, cycloalkenyl, alkynyl, aryl, or heterocyclic substituent(s), or any combination thereof, which substituent(s) can be functionally substituted or unsubstituted. Furthermore, it should also be understood that additional alkoxy containing compounds suitable for amide formation, others than those set forth in detail above, will be recognized by those of ordinary skill in the art or otherwise determined through mere routine experimentation.

Additionally, as set forth above, suitable nitriles for use in the process of the present invention included any compound having the generic formula (II):

$$R—CN \quad (II)$$

wherein R is a hydrogen or any alkyl, cycloalkyl, alkenyl, cycloalkenyl, alkynyl, aryl, or heterocyclic substituent, which substituents can be substituted or unsubstituted. For example, preferred nitrites for use in the process of the present invention include both hydroxy nitrites and alkoxy nitrites; acetonitrile; propionitrile; 2,3-dimethyl-2-(1'-methylethyl) butanenitrile; p-menthanecarbonitrile; and benzonitrile. To this end, it should be understood that additional nitrites suitable for amide formation, other than those set forth in detail above, will be recognized by those of ordinary skill in the art or otherwise determined through mere routine experimentation.

It is also contemplated by the present invention that there are numerous cases when contacting an alkoxy-containing compound with an acid will produce a second alkoxy-containing compound and a second acid. Accordingly, in another aspect of the present invention, one or more of the desired reagents, e.g., the alkoxy-containing compound, is (are) formed in the reaction mixture in situ.

For example, an alkyl mesylate can be obtained in situ by contacting methanesulfochloride with an alkanol. Alternatively, an alkyl chlorosulfate can be obtained in situ by contacting chlorosulfonic acid with an alkanol. Likewise, a dialkyl ether can react with sulfuric acid to provide a monoalkyl sulfate and an alkanol. Similarly, dialkyl sulfate can react with sulfuric acid to provide a monoalkyl sulfate. Furthermore, a trialkyl phosphate can react with a polyphosphoric acid to provide a mixture of acid alkyl phosphates and polyphosphates.

It is also known that alkyl groups can reversibly migrate to sulfuric acid from trialkyl borates or trialkyl phosphates to provide monoalkyl sulfates and partial (acid) esters of boric or phosphoric acid. Alternatively, a dialkyl carbonate can react with sulfuric acid to provide monoalkyl sulfate, alcohol and carbon dioxide. Furthermore, it is also known that alcohols can react with sulfur trioxide to provide monoalkyl sulfates.

Accordingly, depending on the addition sequence and the reaction conditions, it is contemplated by the present invention that such reactions can occur in the presence of a nitrite, before the addition of a nitrite, and/or during the addition of nitrile into the reaction environment. Consequently, in alternative embodiments of the present invention, a nitrile can react with an originally charged alkoxy-containing compound and acid or with a subsequently formed alkoxy-containing compound and acid.

In still a further embodiment of the present invention, it is contemplated that, depending on the reaction conditions, the desired N-monosubstituted amide can either be present in the reaction mixture as a final product, or it can be present in the form of an intermediate complex. In those instances where the desired amide forms as an intermediate reaction complex, a hydrolytic or solvolytic work up may be necessary to recover the product from the reaction mixture.

According to the invention, a hydrolytic or solvolytic workup includes, but is not limited to, treatment with water, aqueous solutions of bases or acids, treatment with alcohols, or any other treatment that aids in and/or results in the recovery of the desired amide from the reaction mixture.

The process of the present invention can also be performed over a wide variety of conditions. Additionally, the process of the present invention can also be performed either continuously or batch-wise. Although the reaction generally proceeds regardless of the temperature, addition sequence, addition rates, and the ratio of the reagents, all these and other parameters can be optimized in order to obtain higher yields of N-monosubstituted amides. Such optimization parameters will be recognized by one of ordinary skill in the art or otherwise achieved through routine experimentation.

The reaction temperature may vary within a wide range, and may even vary during the process, or during different steps of the process. For example, the process can proceed at temperatures of $-20°$ C., $-10°$ C., $0°$ C., $10°$ C., $20°$ C., $30°$ C., $40°$ C., $50°$ C., $60°$ C., $70°$ C., $80°$ C., $90°$ C., $100°$ C., $110°$ C., $120°$ C., $130°$ C., $140°$ C., $150°$ C., $160°$ C., $170°$ C., $180°$ C., $190°$ C., $200°$ C., $210°$ C., $220°$ C., $230°$ C., $240°$ C., or even $250°$ C. In a preferred embodiment, the temperature is not lower than about $-20°$ C. Moreover, the temperature is preferably not greater than about $250°$ C. More preferably, the temperature is not less than about $25°$ C. and not greater than about $180°$ C.

According to the invention, the process can be performed under varying degrees of pressure and reaction time. For example, the process is effective under atmospheric pressure, under increased pressure, or even under vacuum. To this end, the optimum amount of pressure and reaction time will, of course, vary depending on the particular reactants used and will further be recognized by one of ordinary skill in the art or otherwise determined through routine experimentation.

The process can also successfully proceed under varying molar ratios of alkoxy containing compound to nitrile. In a preferred embodiment, the process is preferably performed with a molar ratio of alkoxy-containing compound to nitrile of from about 0.1 to about 50. For example, the ratio of alkoxy-containing compound to nitrile can be 0.1, 0.3, 0.5, 0.7, 0.9, 1, 5, 10, 15, 20, 25, 30, 35, 40, 45, or even 50. In a more preferred embodiment, from about 0.3 to about 10, and even more preferably from about 0.5 to about 5.

The process can also successfully proceed with varying molar ratios of acid to nitrile. In a preferred embodiment, the molar ratio of acid to nitrile is from about 0.01 to about 100. In accordance with this embodiment, the molar ratio of acid to nitrile can be 0.01, 0.05, 0.1, 0.5, 1.0, 5, 10, 15, 20, 25, 30, 35, 40, 45, 50, 55, 60, 65, 70, 75, 80, 85, 90, 95, or even 100. In a more preferred embodiment, the molar ration of acid to nitrile is from about 0.5 to about 10. Alternatively, in a most preferred embodiment, the ratio of acid to nitrile is from about 1 to about 5.

The process of the present invention can also be successfully performed in the presence of an organic or inorganic solvent, or even without a solvent. Examples of suitable solvents include, without limitation, alkanes, chloro- and polychloroalkanes, formamides, and combinations thereof. When the reaction is carried out using an excess of one of the reagents, erg., a nitrile, an alkoxy-containing compound, or an acid, the excess reagent can also serve as the solvent When the present process is performed batchwise, various modes or sequences of addition/mixing of reagents can be used, for example:

1) addition of an alkoxy-containing compound and a solvent into a mixture of a nitrile, acid and another solvent, or optionally, the same sequence without one or both solvents;
2) simultaneous mixing of an acid, a nitrile, an alkoxy-containing compound, and a solvent, or, optionally, the same sequence without the solvent;
3) premixing an acid and an alkoxy-containing compound, with or without a solvent, followed by addition of a nitrile, also with or without a solvent;
4) addition of an acid to a mixture of a nitrile, an alkoxy-containing compound, and an optional solvent.

Similarly, when the process is carried out in a continuous manner, the reagents and optional solvents can be fed into a reactor or reaction environment simultaneously or in any order.

In those embodiments where one or more of the reagents provide two or more functional groups, e.g., a monoalkyl sulfate which provides both an acid and alkoxy functionality, the reagents and optional solvents can also be mixed or fed in any order.

To this end, the process of present invention encompasses any appropriate sequence of addition and/or mixing of two or more appropriate reagents, with or without one or more solvents, in an environment suitable to provide a desired, n-monosubstituted amide, cyclic amide (lactam), and/or functionally substituted di- or polyamide. Furthermore, it should also be understood that, in each case, the optimum sequence of mixing depends on the nature of the starting materials and the solvent used. Accordingly, the optimal sequences will be recognized by those of ordinary skill in the art or otherwise determined through routine experimentation.

After completion of the reaction, the reaction mixture can be worked up in many ways. For example, in an embodiment comprising a hydrolytic work up, the product mixture can be "quenched" with water or an aqueous base, or poured onto ice and neutralized with an aqueous base, then extracted with a solvent. After evaporation of the solvent, the product can be distilled and/or crystallized.

In an embodiment comprising a solvolytic work up, the reaction mixture can be diluted, for example, with an excess of a lower alcohol (methanol, ethanol, etc.), and the product can be crystallized from its alcohol solution, or separated in any other way known in the art. In some cases, the reaction mixture can also be directly distilled to give the desirable product, and in other cases, the product can be obtained from the reaction mixture by direct crystallization followed by an optional purification.

Thus, the present invention is capable of providing a convenient and highly practical process for obtaining desired N-monosubstituted amides, cyclic amides (lactams), functionally substituted di- or polyamides, and cyclic polyamides, by contacting corresponding nitrites with corresponding alkoxy-containing compounds and acids. Additional advantages of the invention will be realized and attained by means of the elements and combinations particularly pointed out in the appended claims.

EXAMPLES

The following examples are put forth so as to provide those of ordinary skill in the art with a complete disclosure and description of how the method for obtaining N-monosubstituted amides is realized, and are intended to be purely exemplary of the invention and are not intended to limit the scope of what the inventors regard as their invention. Efforts have been made to ensure accuracy with respect to numbers (e.g. amounts, temperature, etc.) but some errors and deviations may be present. Unless indicated otherwise, temperature is in ° C. or it is at room temperature, and pressure is at or near atmospheric. Yields of N-monosubstituted amides are calculated on the basis of total amounts of starting nitrites taken into reaction, unless indicated otherwise.

Example 1

Reaction of 2,3-dimethyl-2-(1'-methylethyl) butanenitrile 10 with Chlorosulfonic Acid and Methanol (Addition of an Alcohol to a Mixture of Two Other Reagents)

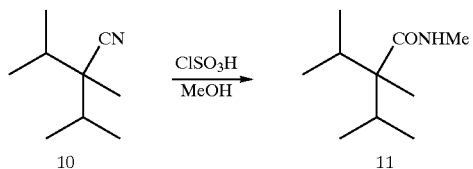

Methanol (21.5 moles) was added to a stirred mixture of 42.4 moles of chlorosulfonic acid and 10.6 moles of nitrile 10 at a temperature maintained within 35–45° C. (with cooling). Outgoing gases were passed through a trap containing dilute aqueous NaOH for absorption of the evolving hydrogen chloride. After completion of the addition of methanol, the reaction mixture was carefully heated to 85° C., stirred 4 hours at this temperature, cooled, diluted with heptane, quenched with an excess of ice and water, and neutralized with aqueous NaOH. The organic layer was separated and rotary evaporated to give 1454.3 g of a crude crystalline material containing, according to GLC, 99.0% of N-methylamide 11 (yield 79.3% of the theory based on nitrile 10). The crude was fractionated in a glass column filled with stainless steel protrusion packing to give 1335.9 g of 99.6% purity N-methylamide 11 (yield 73.4% of the theory).

Examples 2–6

Reaction of 2,3-dimethyl-2-(1'-methylethyl) butanenitrile 10 with Methanol and Sulfuric Acid (Addition of Nitrile to a Mixture of Two Other Reagents)

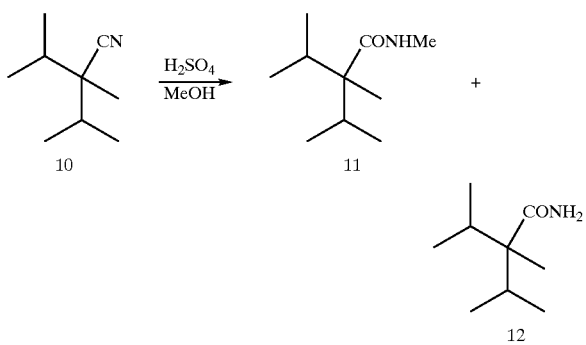

General procedure. Nitrile 10 was added to a solution of methanol in sulfuric acid, and the resulting mixtures were stirred at 100–110° C. for a specified period of time. After a conventional hydrolytic work up, the products were analyzed by GLC. Results are given in Table E2–6.

TABLE E2-6

| Example # | Molar ratio Nitrile 10/ MeOH/H$_2$SO$_4$ | Reaction time, h | Product composition (GLC) | | |
|---|---|---|---|---|---|
| | | | Unreacted nitrile 10 | N-methyl-amide 11 | Amide 12 |
| 2 | 1/1/1 | 3 | 32.15 | 18.2 | 49.2 |
| 3 | 1/2/2 | 3 | 9.6 | 37.1 | 52.3 |
| 4 | 1/4/4 | 3 | 3.2 | 60.2 | 35.0 |
| 5 | 1/6/6 | 1 | 3.9 | 66.9 | 28.0 |
| 6 | 1/8/8 | 1 | 3.0 | 73.2 | 22.6 |

Example 7

Reaction of 2,3-dimethyl-2-(1'-methylethyl) butanenitrile 10 with Methanol and Sulfuric Acid (Addition of Methanol to a Mixture of Two Other Reagents)

Nitrile 10 (0.167 mole) was dissolved in 0.5 mole of concentrated sulfuric acid, then 0.5 mole of methanol was added dropwise, with stirring, over a period of about 15 min, and the temperature of the mixture rose spontaneously to about 80° C. The mixture was heated to 100° C. and stirred at this temperature for 15.3 hours. After a conventional hydrolytic work up, the reaction product contained 4.8% of unreacted nitrile 10, 61.5% of N-methylamide 11, and 33.2% of amide 12.

Example 8

Reaction of 2,3-dimethyl-2-(1'-methylethyl) butanenitrile 10 with Methanol and Fuming Sulfuric Acid Methanol (0.59 mole) was added to 54 g of 27–33% fuming sulfuric acid at about 8° C., the mixture was heated to 95° C. and stirred 1 hour at this temperature. After addition of 0.196 mole of nitrile 10, the temperature rose spontaneously to about 120° C. over a period of 20 min. The mixture was cooled, carefully diluted with water, neutralized with aqueous NaOH, and extracted with heptane. After removal of the heptane, the resulting brownish crystalline product contained 1.3% of unreacted nitrile 10, 78.9% of N-methylamide 11, and 17.3% of amide 12.

Example 9

Reaction of 2,3-dimethyl-2-(1'-methylethyl) butanenitrile 10 with Methanol and Methanesulfonic Acid A mixture of nitrile 10, methanesulfonic acid and methanol in a molar ratio of 1/4/4 was kept for 15.5 hours at 100° C., then hydrolytically worked up. According to GLC analysis, the product contains 32.8% of unreacted nitrile 10, 53.2% of N-methylamide 11, and 13.3% of amide 12.

Example 11

Reaction of 2,3-dimethyl-2-(1'-methylethyl) butanenitrile 10 with Methanol and Phosphoric Acid Nitrile 10 (0.0036 mole) A mixture of 0.016 mole of methanol and 0.02 mole of 100% phosphoric acid was stirred at 95° C. for 30 min. After addition of 0.0036 mole of nitrile 10, the mixture was stirred at the same temperature for 20 hours, then cooled and hydrolytically worked up. GLC analysis showed 97.6% of unreacted nitrile 10, 1.3% of N-methylamide 11, and 0.9% of N-unsubstituted amide 12.

Example 12

Reaction of 2,3-dimethyl-2-(1'-methylethyl) butanenitrile 10 with Methanol and Pyrophosphoric Acid Pyrophosphoric acid (0.022 mole) was dissolved in 0.023 mole of methanol for 5 hours at elevated temperature. After addition of 0.0055 mole of nitrile 10, the mixture was kept at about 100° C. for 40° C. After a conventional hydrolytic work up, the reaction product contained 75.9% of unreacted nitrile 10, 15.4% of N-methylamide 11, and 7.3% of amide 12 (GLC).

Examples 13–15

Reaction of 2,3-dimethyl-2-(1'-methylethyl) butanenitrile 10 with Methyl Methanesulfonate and Methanesulfonic Acid General procedure. A mixture of nitrile 10, methyl methanesulfonate, and methanesulfonic acid is kept at 100° C. for 45 hours, then analyzed by GLC. Reagent ratios and yields are given in Table E13–15.

TABLE E13-15

MMS = methyl methanesulfonate; MSA = methanesulfonic acid.

| Example | Molar ratio of reagents Nitrile 10/MSA/MMS | Unreacted nitrile 10 | N-Methyl-amide 11 | Amide 12 |
|---|---|---|---|---|
| 13 | 1/2/1 | 30.6 | 67.5 | 0.08 |
| 14 | 1/4/4 | 16.3 | 78.8 | 0.2 |
| 15 | 1/1/1 | 22.2 | 74.7 | 0.06 |

Example 16

Reaction of 2,3-dimethyl-2-(1'-methylethyl) butanenitrile 10 with Methyl Acetate and Sulfuric Acid Methyl acetate (0.0135 mole) was dissolved in 0.0153 mole of concentrated sulfuric acid, and the solution was heated at about 100° C. for 3 hours. After addition of 0.0036 mole of nitrile 10, the mixture was kept at 100° C. for another 24 hours. After a hydrolytical work up, the product contained 34.9% of unreacted nitrile 10, 35.1% of N-methylamide 11, and 27.9% of amide 12.

Example 17

Reaction of 2,3-dimethyl-2-(1'-methylethyl) butanenitrile 10 with Trimethylphosphate and Sulfuric Acid at 100° C.

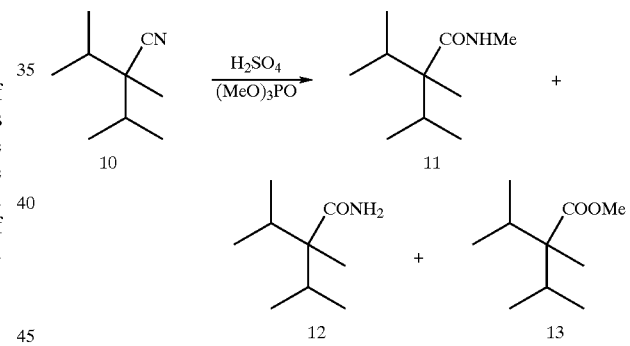

Nitrile 10 (0.083 mole) was added to a stirred at 100° C. solution of 0.246 mole of concentrated sulfuric acid in 0.165 mole of trimethylphosphate. The resulting mixture was stirred at 100° C. for 5.7 hours, cooled to room temperature and hydrolytically worked up to give 13.3 g of crystalline material containing (by GLC) 3.5% of unreacted nitrile 10, 80.6% of N-methylamide 11, 11.0% of amide 12, and 4.0% of by-product methyl ester of 2,3-dimethyl-2-(1'-methylethyl)butanoic acid 13. Yield of N-methylamide 11 75.4% of the theory.

Example 18

Reaction of 2,3-dimethyl-2-(1'-methylethyl) butanenitrile 10 with Trimethylphosphate and Sulfuric Acid at 120° C.

The reaction was carried out as in Example 17, but at 120° C. for 6 hours. According to GLC, the product contained 0.4% of unreacted nitrile 10, 91.7% of N-methylamide 11, 2.8% of amide 12, and 4.5% of ester 13.

Example 19

Reaction of 2,3-dimethyl-2-(1'-methylethyl) butanenitrile 10 with Dimethyl Oxalate and Sulfuric Acid (Addition of Nitrile to a Mixture of Two Other Reagents)

Nitrile 10 (0.025 mole) was added to a solution of 0.1 mole of dimethyloxalate in 0.1 mole of concentrated sulfuric acid. The resulting mixture was heated to 100° C. and stirred at this temperature for 3 hours. After a conventional work up, the product contained 5.5% of unreacted nitrile 10, 59.3% of N-methylamide 11, and 34.4% of amide 12.

Example 20

Reaction of 2,3-dimethyl-2-(1'-methylethyl) butanenitrile 10 with Dimethyl Oxalate and Sulfuric Acid (Addition of Sulfuric Acid to a Mixture of Two Other Reagents).

Sulfuric acid (0.1 mole) was added to a mixture of 0.05 mole of dimethyloxalate in 0.025 mole of nitrile 10. The resulting mixture was heated to 100° C. and stirred at this temperature for 2.5 hours. After a conventional work up, the product contained 1.2% of unreacted nitrile 10, 66.2% of N-methylamide 11, and 31.1% of amide 12.

Example 21

Reaction of Acetonitrile with Chlorosulfonic Acid and 1-butanol

Acetonitrile (0.9 mole) was added to a stirred mixture of 0.78 mole of n-butanol and 0.78 mole of chlorosulfonic acid at 0–5° C. The mixture was heated to 80° C., stirred at this temperature for 2 hours, then cooled, quenched with 20% aqueous NaOH, and extracted with chloroform. The chloroform extract was washed with water and dried over sodium sulfate. After evaporation of the chloroform, the residue was distilled to give 11.9 g of a product containing 38.5% of N-n-butylacetamide, which was identified by GLC and GC/MS by comparison with an authentic sample. Yield of N-n-methylacetamide 5.1% of the theory based on n-butanol.

Example 22

Reaction of Benzonitrile with Sulfuric Acid and Dimethylsulfate

A mixture of 0.78 mole of dimethylsulfate and 0.78 mole of sulfuric acid was stirred 10 min at 110° C., then cooled to 10° C. After addition of 0.78 mole of benzonitrile at 10° C., the mixture was heated to 100° C., stirred 1 hour at this temperature, cooled, quenched with excess of ice, neutralized with 20% aqueous NaOH, and extracted with chloroform. The chloroform extract was washed with water, dried over sodium sulfate, and evaporated to give 15.2 g of an oil containing 24.4% of N-methylbenzamide (yield 22% of the theory), which was identified by GLC by comparison with an authentic sample.

Example 23

Reaction of p-menthane-3-carbonitrile 14 with Chlorosulfonic Acid and Ethanol

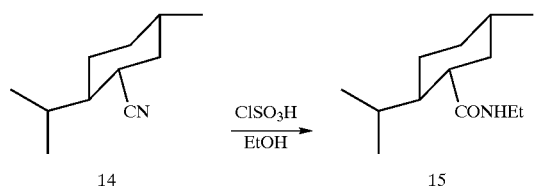

Ethanol (0.2 mole) was added to a stirred mixture of 0.4 mole of chlorosulfonic acid and 0.1 mole of nitrile 14 over a period of 20 minutes at 30–35° C. The reaction mixture was heated to 85° C., stirred at this temperature for 3 hours, cooled, quenched with excess of ice, and extracted with toluene. The toluene extract was neutralized with 20% aqueous NaOH, washed with water, and dried with sodium sulfate. The toluene was evaporated to give 4.6 g of a product containing 27.9% of N-ethylamide 15, which was identified by GLC by comparison with an authentic sample. Yield of N-ethylamide 15— 6.1% of the theory based on nitrile 14.

Example 24

Reaction of Methyl Ester of 2,2-diisopropylcyanoacetic acid 16 with Sulfuric Acid and Methanol

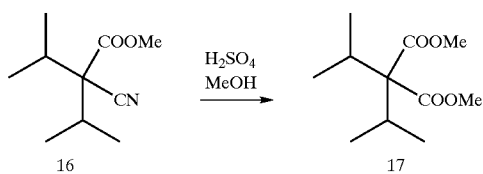

Methyl ester of 2,2-diisopropylcyanoacetic acid 16 (0.628 mole) was added to a mixture of 2.5 mole of concentrated sulfuric acid and 2.5 mole of ethanol. The mixture was stirred at 100° C. for 11.5 hours, diluted with water, neutralized with 10% aqueous NaOH, and extracted with chloroform. After removal of the chloroform, the product was distilled to give 114.2 g of a crystalline material containing 69.7% (0.37 mole) of N-methylamide 17 and 21.3% (0.133 mole) of starting ester 16. Yield of N-methylamide 17 based on reacted ester 16 is 74.7% of the theory. The product was recrystallized from heptane to give 99%+pure N-methylamide 17, m.p. 89° C.; $^1$H NMR (300 MHz, CDCl3, $\delta$ ppm): 0.87 d, J=6.9 Hz (6H, Me$_2$C), 0.89 d, J=6.9 Hz (6H, Me$_2$C), 2.60 septet J=6.9 Hz (2H, 2Me$_2$C), 2.79 d, J=4.7 Hz (3H, MeNH), 3.71 s (3H, MeO), 7.76 br. s (1H, NH).

Example 25

Reaction of Ethyl Ester of 2,2-diisopropylcyanoacetic acid 18 with Sulfuric Acid and Methanol

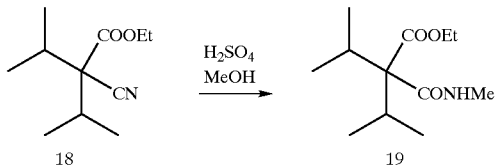

Ethyl ester of 2,2-diisopropylcyanoacetic acid 18 (0.578 mole) was added to a mixture of 2.5 mole of concentrated sulfuric acid and 2.5 mole of methanol. The mixture was stirred at 100° C. for 17 hours, diluted with water, neutralized with 10% aqueous NaOH, and extracted with chloroform. After removal of the chloroform, the product was distilled to give 114.4 g of a material containing 69.7% of N-methylamide 19 and 19.2% of starting ester 18. Yield of N-methylamide 19 based on reacted ester 18 is 74.5% of the theory. Compound 19 was further purified by distillation. $^1$H NMR (270 MHz, CDCl$_3$, $\delta$ ppm): 0.87 d, J=6.8 Hz (6H, Me$_2$C), 0.89 d, J=6.8 Hz (6H, Me$_2$C), 1.27 t, J=7.3 Hz (3H, MeCH$_2$), 2.59 septet, J=6.8 Hz (2H, 2Me$_2$CH), 2.77 d, J=4.9 Hz (3H, MeNH), 4.17 q, J=7.3 Hz, 7.83 br.s (1H, NH).

Example 26

Reaction of Ethyl Ester of 2,2-diisopropylcyanoacetic Acid 18 with Sulfuric Acid and Ethanol

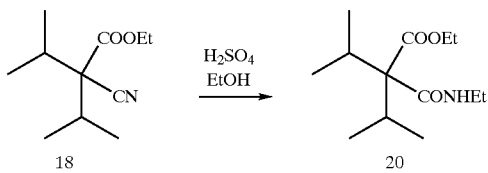

Ethyl ester of 2,2-diisopropylcyanoacetic acid 18 (0.31 mole) was added to a mixture of 1.25 mole of concentrated sulfuric acid and 1.25 mole of ethanol. The mixture was stirred at 100° C. for 17 hours, diluted with water, neutralized with 10% aqueous NaOH, and extracted with chloroform. After removal of the chloroform, the product was distilled to give 54.1 g of a material containing 62.9% of N-methylamide 20 and 22.7% of starting ester 18. Yield of N-methylamide 20 based on reacted ester 18 is 56.5% of the theory. Compound 20 was further purified by distillation. $^1$H NMR (270 MHz, CDCl$_3$, $\delta$ ppm): 0.88 d, J=6.8 Hz (6H, Me$_2$C), 0.90 d, J=6.8 Hz (6H, Me$_2$C), 1.11 t, J=7 Hz (3H, MeCH$_2$), 1.25 t, J=7 Hz (3H, MeCH$_2$), 2.60 septet, J=6.8 Hz (2H, 2CHMe$_2$), 3.28 m (2H, MeCH$_2$NH), 4.17 q, J=7 Hz (2H, MeCH$_2$O), 7.83 br. s (1H, NH).

Example 27

Reaction of 2,3-dimethyl-2-(1'-methylethyl) butanenitrile 10 with an about Equimolar Amount of Monomethylsulfate Prepared from Dimethyl Sulfate and Sulfuric Acid A mixture of 0.52 mole of dimethylsulfate and 0.5 mole of concentrated sulfuric acid was stirred at 100° C. for 1 hour, then the temperature was increased to 115° C. One mole of nitrile 10 was added dropwise over a period of 35 min, and the mixture was stirred at 115° C. for 18 hours. The resulting viscous mixture was cooled and hydrolytically worked up. GLC analysis of the product showed 46.2% of unreacted nitrile 10, 38.6% of N-methylamide 11, 0.75% of amide 12, and 13.4% of ester 13.

Example 28

Reaction of 2,3-dimethyl-2-(1'-methylethyl) butanenitrile 10 with an about Quadruple Excess of Monomethylsulfate Prepared from Dimethyl Sulfate and Sulfuric Acid A mixture of 0.52 mole of dimethylsulfate and 0.5 mole of concentrated sulfuric acid was stirred at 100° C. for 2 hours. After addition of 0.252 mole of nitrile 10, the mixture was stirred at about 100° C. for 3 hours, cooled, and hydrolytically worked up. According to GLC, the product contained 0.8% of unreacted nitrile 10, 92.4% of N-methylamide 11, and 4.6% of amide 12. Amount of by-product ester 13 was insignificant (0.09%).

Example 29

Reaction of 2,3-dimethyl-2-(1'-methylethyl) butanenitrile 10 with Monomethylsulfate Prepared from Chlorosulfonic Acid and Methanol Methanol (32 moles) was added over a period of 8.5 hours at 0–+5° C. to 32 moles of chlorosulfonic acid. After evolution of gaseous HCl subsided, the mixture was allowed to warm up to room temperature and left to stay at room temperature for about 65 hours. Nitrile 10 (8 moles) was added at 100° C. for about 1 hour, the mixture was stirred for 2.5 hours, neutralized with aqueous NaOH, and extracted with heptane. Evaporation of heptane gave 1091 g of a crude material containing (by GLC) 94.4% of N,2,3-trimethyl-2-(1'-methylethyl)butaneamide 11. The crude material was fractionated in a 4'-column (internal diameter 1"), filled with stainless steel protrusion packing, to give 874.38 g of 99.5% purity N,2,3-trimethyl-2-(1'-methylethyl)butanamide 11 (yield of purified product 63.5% of the theory).

Example 30

Reaction of 2,3-dimethyl-2-(1'-methylethyl) butanenitrile 10 with Monomethylsulfate Prepared from Sulfur Trioxide and Methanol Methanol (0.1125 mole) was added to 0.1125 mole of sulfur trioxide at below 0° C., then the mixture was allowed to warm up to room temperature and was stirred at room temperature for 1 hour. After addition of 0.1122 mole of nitrile 10, the mixture was stirred at 100° C. for 16 hours, cooled, and hydrolytically worked up. According to GLC analysis, the product contained 45.9% of unreacted nitrile 10, 38.7% of N-methylamide 11, 1.0% of amide 12, and 13.7% of ester of 13.

Example 31

Reaction of 2,3-dimethyl-2-(1'-methylethyl) butanenitrile 10 with Monomethylsulfate Prepared from a Dimethylformamide Complex of Sulfur Trioxide and Methanol Methanol (0.00625 mole) was added to 0.0065 mole of dimethylformamide complex of sulfur trioxide, and the temperature of the mixture spontaneously rose to 60° C. After addition of 0.0036 mole of nitrile 10, the mixture was kept 2 hours at 120° C., then 64 hours at 100° C. After a conventional hydrolytical work up, the product contained 71.0% of unreacted nitrile 10, 27.5% of N-methylamide 11, 0.04% of amide 12, and 1.2% of ester 13.

After addition of nitrile 10, the mixture was stirred at the given temperature for a given period of time, cooled, diluted with water, neutralized with aqueous NaOH, and extracted with heptane. The heptane was evaporated, and the remaining product was analyzed by GLC. Molar ratios of reagents, reaction conditions, and results of GLC analyses are given in Table E34–37.

TABLE E34–37

10 = nitrile 10; DMC = dimethylcarbonate; SA = sulfuric acid

| | | | | Composition of the product, % (GLC) | | | |
|---|---|---|---|---|---|---|---|
| Example # | Molar ratio 10/DMC/SA | Reaction temperature, ° C. | Reaction time, min | Unreacted 10 | N-methyl amide 11 | Amide 12 | Ester 13 |
| 34 | 1/4/4 | 105 and 120 | 2 and 0.5 | 0.9 | 88.3 | 10.2 | 0.1 |
| 35 | 1/2/4 | 100 | 5 | 2.2 | 78.1 | 19.4 | 0.3 |
| 36 | 1/4/2 | 110 | 4 | 2.7 | 72.6 | 22.0 | 2.4 |
| 37 | 1/8/4 | 100 | 4 | 0.9 | 87.9 | 10.3 | 0.5 |

Example 32

Reaction of 2,3-dimethyl-2-(1'-methylethyl) butanenitrile 10 with Monomethylsulfate Prepared from Sulfuric acid and Trimethylphosphate A mixture of 0.5 mole of concentrated sulfuric acid and 0.34 mole of trimethylphosphate was stirred for 1 hour at 100° C. in vacuum (~3 mm Hg). Then, 0.172 mole of nitrile 10 was added. at atmospheric pressure, and the resulting mixture was stirred at 100° C. for 6.8 hours. The mixture was cooled, diluted with water, neutralized with aqueous NaOH, and extracted with heptane. Evaporation of heptane gave 32.0 g of a material containing, according to GLC, 13.4% of unreacted nitrile 10, 75.9% of N-methylamide 11, 5.3% of amide 12, and 4.0% of ester 13. Yield of N-methylamide 11 82.3%.

Example 33

Reaction of 2,3-dimethyl-2-(1'-methylethyl) butanenitrile 10 with Monomethylsulfate Prepared from Sulfuric Acid and Trimethylborate A mixture of 0.54 mole of concentrated sulfuric acid and 0.48 mole of trimethylborate was stirred 0.5 h at 100° C. After addition of 0.215 mole of nitrile 10, the stirring at 100° C. continued for 8 hours. The mixture was cooled, diluted with water, neutralized with aqueous NaOH, and extracted with heptane. Evaporation of heptane gave 22.4 g of a product containing (by GLC) 7.2% of unreacted nitrile 10, 81.3% of N-methylamide 11, and 11.3% of amide 12. Yield of of N-methylamide 11 49.5% of the theory.

Examples 34–37

Reaction of 2,3-dimethyl-2-(1'-methylethyl) butanenitrile 10 with Monomethylsulfate Prepared from Sulfuric Acid and Dimethylcarbonate General procedure. Dimethylcarbonate was added dropwise at 100° C. to concentrated sulfuric acid slowly enough as to keep the formation of gaseous $CO_2$ under control, and the resulting mixture was kept at 100° C. for 2–3 hours.

Example 38

Reaction of 2,3-dimethyl-2-(1'-methylethyl) butanenitrile 10 with Trimethylphosphate and Methanesulfonic Acid at 140° C.

A mixture of 10 moles of methanesulfonic acid, 3.57 moles of trimethylphosphate, and 2.126 moles of nitrile 10 was stirred at 140° C. for 5 hours, cooled, hydrolytically Worked up, extracted with heptane, evaporated and distilled to give 326.1 g of 97.5% pure crystalline N-methylamide 11 (1.856 moles) and 20.2 g of an intermediate fraction containing 61.1% of N-methylamide 11 (0.072 mole). Yield of N-methylamide 11 90.7% of the theory.

Example 39

Reaction of 2,3-dimethyl-2-(1'-methylethyl) butanenitrile 10 with Dimethyl Carbonate and Polyphosphoric Acid A mixture of 800 g of "115%" polyphosphoric acid, 1.78 moles of dimethylcarbonate, and 1.90 moles of nitrile 10 was heated to 140° C., stirred at this temperature for 10 hours, cooled, hydrolytically worked up, extracted with heptane, evaporated and distilled to give 312.6 g of 98% pure crystalline N-methylamide 11 (1.789 moles) and 3.4 g of an intermediate fraction containing 39.8% of N-methylamide 11 (0.008 mole). Yield of N-methylamide 11 94.6% of the theory.

Example 40

Reaction of 2,3-dimethyl-2-(1'-methylethyl) butanenitrile 10 with Dimethyl Carbonate and Partially Dilute Polyphosphoric Acid Polyphosphoric acid ("115%", 124.7 g) was diluted with 4.2 g of water and mixed with 0.333 mole of dimethylcarbonate and 0.28 mole of nitrile 10. The mixture was slowly heated to 140° C., stirred at this temperature for 8 hours, cooled, hydrolytically worked up, and extracted with heptane. Crystallization of the product from heptane solution gave 42.10 g of 99.5% pure N-methylamide 11 (first crop), 1.66 g of 98.85% pure N-methylamide 11 (second crop), and 0.43 g of 98.4% pure N-methylamide 11 (third crop). Yield of N-methylamide 11 91.6% of the theory.

Example 41

Reaction of 2,3-dimethyl-2-(1'-methylethyl) butanenitrile 10 with Methanol and Polyphosphoric Acid Polyphosphoric acid ("115%", 900 g) was added at 25–90° C. to a mixture of 2.126 moles of nitrile 10 and 4.31 moles of methanol. The mixture was heated to 150° C. and stirred at this temperature for about 10 hours, cooled to 80–90° C., diluted with 500 ml of water, neutralized to pH~5.5 with 50% aqueous NaOH, and extracted with heptane. The heptane extract was washed with ~20%NaOH and with water.

The reaction was repeated two more times, all three heptane extracts were combined, evaporated and distilled to give 1018.2 g of 98.64% pure N-methylamide 11. Yield of N-methylamide 11 91.9% of the theory.

Example 42

Reaction of 2,3-dimethyl-2-(1'-methylethyl) butanenitrile 10 with Methyl Polyphosphate Obtained from Methanol and Phosphoric Acid Preparation of methyl polyphosphate. A mixture of 100 g of 85% phosphoric acid (0.87 mole) and 50 g of methanol was heated and methanol was distilled under atmospheric pressure to give 54 g of aqueous methanol (13.4% of water by Karl Fischer). Another 50 g of methanol was added to the remaining acid, and the distillation was repeated (49 g of 7.7% aqueous methanol). After 6 such cycles, followed by heating 1 hour at 150–170° C. at 80 mm Hg, the weight of methyl polyphosphate in the flask was 87.4 g.

Synthesis of 11. A mixture of 55 g of the methyl polyphosphate obtained as above and 0.097 mole of nitrile 10 was stirred at 140° C. for 11.5 hours, then analyzed by GLC, which showed that the product contained 95.8% of N-methylamide 11, 2.4% of unreacted nitrile 10, and 0.73% of unsubstituted amide 12.

Example 43

Reaction of p-menthane-3-carbonitrile 14 with Methanesulfonic Acid and Ethylmethanesulfonate A mixture of 0.12 mole of p-menthane-3-carbonitrile 14, 0.5 mole of methanesulfonic acid, and 0.5 mole of ethyl methanesulfonate (ethyl mesylate) was stirred 6.5 hours at 140° C., cooled, hydrolytically worked up, and extracted with heptane. After evaporation of heptane, the product was distilled to give 22.5 g of 97.9% pure N-ethylamide 15 (yield 86.9% of the theory).

Example 44

Reaction of p-menthane-3-carbonitrile 14 with Polyphosphoric Acid and Triethylphosphate A mixture of 3 mmol of p-menthane-3-carbonitrile 14, 1.5 g of "115%" polyphosphoric acid, and 5.5 mmol of triethylphosphate was heated 7 hours at 140° C., cooled, hydrolytically worked up, and analyzed by GLC, which showed a complete conversion of nitrile 14 into N-ethylamide 15.

While the present invention has been described in terms of various embodiments thereof, it will be understood that various modifications, substitutions, omissions, and other changes can be made without departing from the spirit thereof. Thus, the invention is limited only by the scope of the following claims including equivalents thereof.

What is claimed is:

1. A process for obtaining an amide of the general formula:

$$R-(CO)-NH-CH_2-X$$

comprising reacting a nitrile of the general formula:

$$R-CN$$

with:

a) an acid; and b) an alkoxy-containing compound comprising at least one alkoxy functionality of the general formula:

$$-OCH_2-X$$

wherein R is a hydrogen or an alkyl, cycloalkyl, alkenyl, cycloalkenyl, alkynyl, aryl, or heterocycle, which substituents are substituted or unsubstituted; wherein X is hydrogen or a radical having the general formula $-CHR^1R^2$ wherein $R^1$ and $R^2$ independently or collectively represent hydrogen or an alkyl, cycloalkyl, alkenyl, cycloalkenyl, alkynyl, aryl, or heterocyclic substituent, or any combination thereof, and which substituents are substituted or unsubstituted; and wherein the alkoxy-containing compound is not a mono alkyl sulfate or dialkyl sulfate.

2. The process of claim 1 wherein R is substituted with a functional substituent.

3. The process of claim 1 wherein X is substituted with a functional substituent.

4. The process of claim 1, wherein the acid is a Bronsted acid.

5. The process of claim 1, wherein the acid is a Lewis acid.

6. The process of claim 1, wherein the acid is chlorosulfonic acid, pyrophosphoric acid, polyphosphoric acid, methanesulfonic acid, sulfur trioxide, complexes of sulfur trioxide, or any mixture thereof.

7. The process of claim 1, wherein the alkoxy containing compound is a primary alcohol, a glycol, a diglycol, a polyglycol, an ether, an ester, an orthoester, an acetal, or a ketal.

8. The process of claim 7, wherein the alkoxy containing compound is methanol, ethanol, 1-propanol, 1-butanol, 2-methyl-1-propanol, ethylene glycol, diethylene glycol, or polyethylene glycol.

9. The process of claim 1 wherein the alkoxy-containing compound is an alkyl mesylate, an alkyl arylsulfonate, an alkyl chlorosulfate, a trialkyl borate, a trialkyl phosphate, an acid alkyl phosphate, a dialkyl pyrophosphate, an alkyl polyphosphate, an alkylorthosilicate, an alkylorthotitanate, an alkylorthocarbonate, a dialkylcarbonate, a dialkylacetal, a dialkylketal, a dialkyl ether, a glycol ether, an arylalkyl ether, or an alkyl ester.

10. The process of claim 1 wherein the alkoxy-containing compound forms in the reaction mixture in situ.

11. The process of claim 10 wherein the alkoxy-containing compound is an alkyl mesylate and it is obtained by contacting methanesulfochloride with an alkanol.

12. The process of claim 10 wherein the alkoxy-containing compound is an alkyl chlorosulfate and it is obtained by contacting chlorosulfonic acid and alkanol.

13. The process of claim 1 wherein the nitrile is acetonitrile, propionitrile, 2,3-dimethyl-2-(1'-methylethyl) butanenitrile, p-menthanecarbonitrile, or benzonitrile.

14. The process of claim 1 wherein the molar ratio of alkoxy-containing compound to nitrile is from about 0.1 to about 50, and the molar ratio of acid to nitrile is from about 0.01 to about 100, and the contacting is carried out at a temperature from about minus 20° C. to about plus 250° C.

15. The process of claim 1 wherein the molar ratio of alkoxy-containing compound to nitrile is from about 0.5 to about 5, and the contacting is carried out at a temperature from about plus 25° C. to about plus 180° C.

16. The process of claim 1 wherein the molar ratio of acid to nitrile is from about 1 to about 5, and the contacting is carried out at a temperature from about plus 25° C. to about plus 180° C.

17. The process of claim 1 performed in the presence of an organic or inorganic solvent.

18. The process of claim 1 which process is performed batch-wise.

19. The process of claim 1 which process is performed continuously.

20. The process of claim 1 wherein a) and b) are introduced sequentially to the nitrile.

21. The process of claim 1 wherein a) and b) are introduced simultaneously to the nitrile.

22. The process of claim 1 wherein acid is added to a mixture of nitrile and alkoxy-containing compound.

23. The process of claim 1 wherein the nitrile is added to a mixture of acid and alkoxy-containing compound.

24. The process of claim 1 wherein the alkoxy-containing compound is added to a mixture of nitrile and acid.

25. The process of claim 1 wherein the nitrile, a) and b) are simultaneously introduced into a reactor environment.

26. A process for obtaining an amide of the general formula:

comprising reacting a nitrile of the general formula:

with an acid alkyl phosphate comprising at least one alkoxy functionality of the generic formula XCH$_2$—O— and one or more acid phosphate functionalities of the generic formula:

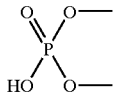

wherein:

R is hydrogen or an alkyl, cycloalkyl, alkenyl, cycloalkenyl, alkynyl, aryl, or heterocyclic substituent, which substituent is substituted or unsubstituted, and X is hydrogen or a radical having the general formula —CHR$^1$R$^2$ wherein R$^1$ and R$^2$ individually or collectively represent hydrogen or an alkyl, cycloalkyl, alkenyl, cycloalkenyl, alkynyl, aryl, or heterocyclic substituent, or any combination thereof, and which substituents are substituted or unsubstituted.

27. The process of claim 26 wherein the acid alkyl phosphate forms in the reaction mixture in situ.

28. The process of claim 1, further comprising a hydrolytic or solvolytic work up.

29. The process of claim 26, further comprising a hydrolytic or solvolytic work up.

30. The process of claim 1 wherein the nitrile is a hydroxynitrile or an alkoxynitrile capable of reacting as both the nitrile and the alkoxy-containing compound.

31. The process of claim 1 wherein the nitrile contains two or more nitrile groups, and the alkoxy-containing compound contains two or more alkoxy groups.

* * * * *